US009044740B2

(12) United States Patent
Maloisel et al.

(10) Patent No.: US 9,044,740 B2
(45) Date of Patent: Jun. 2, 2015

(54) PURIFICATION OF IMMUNOGLOBULINS

(75) Inventors: Jean-Luc Maloisel, Uppsala (SE);
Bo-Lennart Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 579 days.

(21) Appl. No.: 12/594,002

(22) PCT Filed: Mar. 20, 2008

(86) PCT No.: PCT/SE2008/000212
§ 371 (c)(1),
(2), (4) Date: Sep. 30, 2009

(87) PCT Pub. No.: WO2008/121042
PCT Pub. Date: Oct. 9, 2008

(65) Prior Publication Data
US 2010/0121035 A1 May 13, 2010

(30) Foreign Application Priority Data
Mar. 30, 2007 (SE) ...................................... 0700842

(51) Int. Cl.
C07K 16/00 (2006.01)
C07H 1/00 (2006.01)
B01D 15/38 (2006.01)
B01D 15/08 (2006.01)
B01J 20/289 (2006.01)
B01D 15/32 (2006.01)
B01J 20/286 (2006.01)
B01J 20/32 (2006.01)
C07K 1/20 (2006.01)
B01J 20/26 (2006.01)
B01D 15/36 (2006.01)

(52) U.S. Cl.
CPC .............. *B01J 20/289* (2013.01); *B01D 15/32* (2013.01); *B01D 15/327* (2013.01); *B01D 15/361* (2013.01); *B01D 15/3804* (2013.01); *B01D 15/3847* (2013.01); *B01J 20/286* (2013.01); *B01J 20/3285* (2013.01); *C07K 16/00* (2013.01); *C07K 1/20* (2013.01); *B01J 20/262* (2013.01); *B01J 20/267* (2013.01); *B01J 20/3212* (2013.01); *B01J 20/3219* (2013.01); *B01J 20/3251* (2013.01); *B01J 20/3272* (2013.01); *B01J 20/328* (2013.01); *B01J 2220/54* (2013.01); *B01J 2220/58* (2013.01)

(58) Field of Classification Search
None
See application file for complete search history.

(56) References Cited

U.S. PATENT DOCUMENTS

| 4,725,355 A | 2/1988 | Yamamoto et al. |
| 8,685,248 B2 * | 4/2014 | Glad et al. .................... 210/635 |
| 2003/0027809 A1 * | 2/2003 | Kano et al. .............. 514/210.09 |
| 2006/0063822 A1 * | 3/2006 | Weinstein et al. ........... 514/414 |
| 2010/0151581 A1 * | 6/2010 | Glad et al. ....................... 436/86 |

FOREIGN PATENT DOCUMENTS

| WO | WO 96/09116 | 3/1996 |
| WO | WO 03/046063 | 6/2003 |
| WO | WO 2005/061543 | 7/2005 |
| WO | WO 2006/001771 | 1/2006 |
| WO | WO 2007/064281 | 6/2007 |

OTHER PUBLICATIONS

DuBois, "Amination of aryl sulfamate esters. A convenient general synthesis of aliphatic sulfamides," J. Org. Chem., 1980, 45 (26), pp. 5373-5375.*
Reitz et al., "The role of sulfamide derivatives in medicinal chemistry: a patent review (2006-2008)," Expert Opin. Ther. Patents, Oct. 2009, vol. 19, No. 10, pp. 1449-1453.*
Winum et al., "Therapeutic potential of sulfamides as enzyme inhibitors," Med. Res. Rev., 2006; vol. 26, pp. 767-792.*
Arshady, R., "Styrene based polymer supports developed by suspension polymerization", Chimica e L'Industria, 70 (9), 70-75 (1988).
Dahri, L., et al., "Affinity of Human Anti-Factor VIII Antibodies for Functional Polystyrene Supports", Journal of Molecular Recognition, 9(5-6), 401-406 (1996).
Dourges, M., et al., "Affinity chromatography of fibroblast growth factors on substituted polystyrene", Journal of Chromatography, 526(1), 35-45 (1990).
Hjerten, S., "The Preparation of Agarose Spheres for Chromatography of Molecules and Particles", Biochim Biophys Acta, 79(2), 393-398 (1964).
Knudsen, K., et al., "Sulfone-Aromatic Ligands for Thiophilic Adsorption Chromatography: Purification of Human and Mouse Immunoglobulins", Analytical Biochemistry, 201, 170-177 (1992).
Liu, Y., et al., "Novel sulfamethazine ligand used for one-step purification of immunoglobulin G from human plasma", Journal of Chromatography B, 792(2), 177-185 (2003).
Porath, J., et al., "Thiophilic adsorption—a new method for protein fractionation", FEBS Letters, 185(2), 306-310 (1985).
Porath, J., et al., "A New Kind of 'Thiophilic' Electron-Donor-Acceptor Adsorbent", Makromol. Chem., Makromol. Symp., 17, 359-371 (1988).
Schwarz, A., et al., "Novel heterocyclic ligands for the thiophilic purification of antibodies", Journal of Chromatography B, 664, 83-88 (1995).

* cited by examiner

Primary Examiner — Galina Yakovleva
(74) Attorney, Agent, or Firm — Parks Wood LLC

(57) ABSTRACT

The present invention relates to a separation matrix comprised of a porous or non-porous support to which ligands have been immobilized, wherein said ligands comprise at least one aliphatic sulfamide. The invention also relates to a chromatography column that contains the described separation matrix, as well as to a method of isolating immunoglobulins, such as IgG, Fab fragments, fusion proteins containing immunoglobulins etc, by adsorption to a separation matrix that comprises the aliphatic sulfamide ligands of the invention.

23 Claims, 2 Drawing Sheets

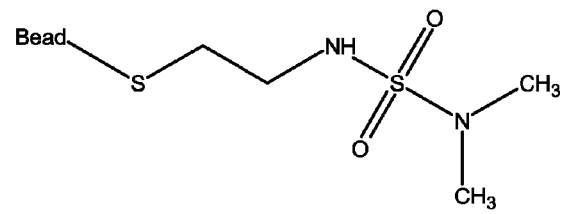
Fig. 1. Ligand structure of the dimethyl sulfamide ligand
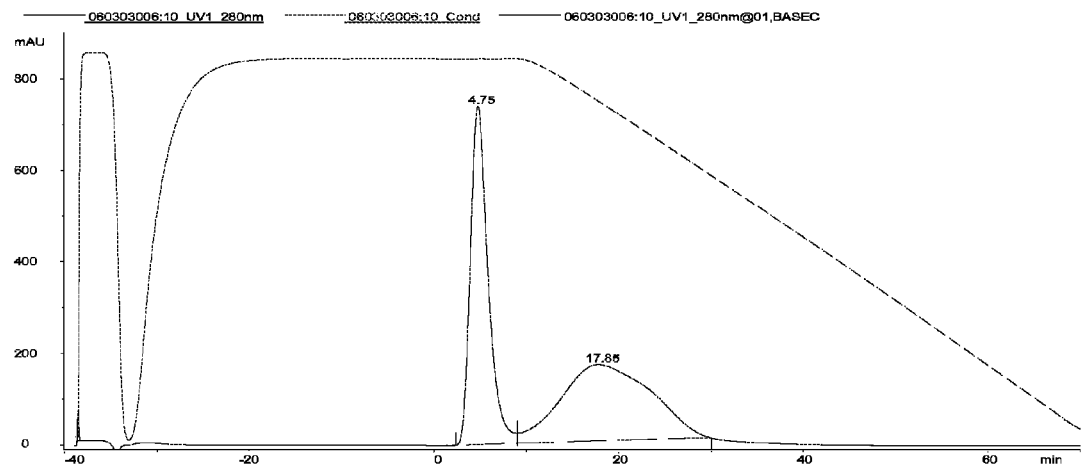
Fig. 2. Separation of α-chymotrypsinogen, lysozyme and ribonuclease.

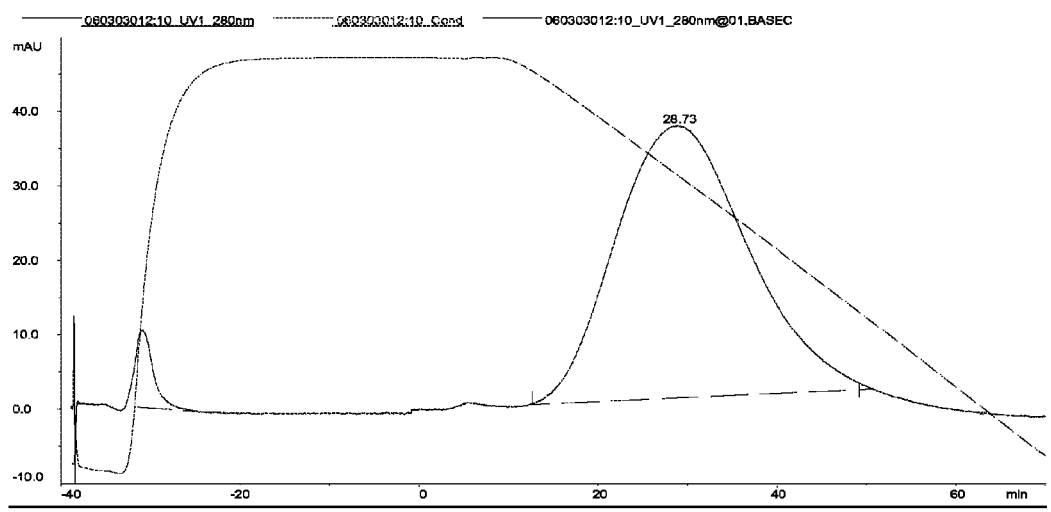
Fig. 3. /min Separation of IgG.

PURIFICATION OF IMMUNOGLOBULINS

CROSS-REFERENCE TO RELATED APPLICATIONS

This application is a filing under 35 U.S.C. §371 and claims priority to international patent application number PCT/SE2008/000212 filed Mar. 20, 2008, published on Oct. 9, 2008, as WO 2008/121042, which claims priority to patent application number 0700842-8 filed in Sweden on Mar. 30, 2007.

FIELD OF THE INVENTION

The present invention relates to the field of immunoglobulin preparation, and more specifically to a separation matrix for isolation of immunoglobulins. The invention also encompasses a chromatography column that comprises the novel matrix and a method of isolating antibodies.

BACKGROUND OF THE INVENTION

The immune system is composed of many interdependent cell types that collectively protect the body from bacterial, parasitic, fungal, viral infections and from the growth of tumour cells. The guards of the immune system are macrophages that continually roam the bloodstream of their host. When challenged by infection or immunisation, macrophages respond by engulfing invaders marked with foreign molecules known as antigens. This event, mediated by helper T cells, sets forth a complicated chain of responses that result in the stimulation of B-cells. These B-cells, in turn, produce proteins called antibodies, which bind to the foreign invader. The binding event between antibody and antigen marks the foreign invader for destruction via phagocytosis or activation of the complement system. Five different classes of antibodies, or immunoglobulins, exist: IgA, IgD, IgE, IgG, and IgM. They differ not only in their physiological roles but also in their structures. From a structural point of view, IgG antibodies are a particular class of immunoglobulins that have been extensively studied, perhaps because of the dominant role they play in a mature immune response.

The biological activity, which the immunoglobulins possess, is today exploited in a range of different applications in the human and veterinary diagnostic, health care and therapeutic sector. In fact, in the last few years, monoclonal antibodies and recombinant immunoglobulin constructs have become the largest class of proteins currently investigated in clinical trials and receiving FDA approval as therapeutics and diagnostics. Complementary to expression systems and production strategies, purification protocols are designed to obtain highly pure antibodies in a simple and cost-efficient manner.

Traditional methods for isolation of immunoglobulins are based on selective reversible precipitation of the protein fraction comprising the immunoglobulins while leaving other groups of proteins in solution. Typical precipitation agents being ethanol, polyethylene glycol, lyotropic i.e. anti-chaotropic salts such as ammonium sulphate and potassium phosphate, and caprylic acid. Typically, these precipitation methods are giving very impure products while at the same time being time consuming and laborious. Furthermore, the addition of the precipitating agent to the raw material makes it difficult to use the supernatant for other purposes and creates a disposal problem, which is particularly relevant when speaking of large-scale purification of immunoglobulins.

Ion exchange chromatography is another well-known method of protein fractionation frequently used for isolation of immunoglobulins. However, since the charged ion exchange ligands will react with all oppositely charged compounds, the selectivity of ion exchange chromatography may be somewhat lower than other chromatographic separations.

Protein A and Protein G affinity chromatography are popular and widespread methods for isolation and purification of immunoglobulins, particularly for isolation of monoclonal antibodies, mainly due to the ease of use and the high purity obtained. Used in combination with ion exchange, hydrophobic interaction, hydroxyapatite and/or gel filtration steps, especially protein A-based methods have become the immunoglobulin purification method of choice for many biopharmaceutical companies. However, despite their common usage, there is a growing need and demand for effective alternatives addressing familiar problems associated with protein A-based media, such as cost, leakage and instability at increased pH values.

Hydrophobic interaction chromatography (HIC) is also a method widely described for isolation of immunoglobulins. However, hydrophobic matrices require an addition of lyotropic salts to the raw material to make the immunoglobulin bind efficiently. The bound immunoglobulin is released from the matrix by lowering the concentration of lyotropic salt in a continuous or stepwise gradient. If a highly pure product is the object, it is recommended to combine the hydrophobic chromatography with a further step. Thus, a disadvantage of this procedure is the necessity to add lyotropic salt to the raw material as this gives a d problem and thereby increased cost to the large-scale user. For other raw materials than cell culture supernatants such as whey, plasma, and egg yolk the addition of lyotropic salts to the raw materials would in many instances be prohibitive in large-scale applications as the salt could prevent any economically feasible use of the immunoglobulin depleted raw material. An additional problem in large-scale applications would be the disposal of several thousand liters of waste.

Thiophilic adsorption chromatography was introduced by J. Porath in 1985 (J. Porath et al; FEBS Letters, vol. 185, p. 306, 1985) as a new chromatographic adsorption principle for isolation of immunoglobulins. In this paper, it is described how divinyl sulphone activated agarose coupled with various ligands comprising a free mercapto-group show specific binding of immunoglobulins in the presence of 0.5 M potassium sulphate, i.e. a lyotropic salt. It was postulated that the sulphone group, from the vinyl sulphone spacer, and the resulting thioether in the ligand was a structural necessity to obtain the described specificity and capacity for binding of antibodies. It was however later shown that the thioether could be replaced by nitrogen or oxygen if the ligand further comprised an aromatic radical (K. L. Knudsen et al, Analytical Biochemistry, vol. 201, p. 170, 1992). Although the matrices described for thiophilic chromatography generally show good performance, they also have a major disadvantage in that it is needed to add lyotropic salts to the raw material to ensure efficient binding of the immunoglobulin, which is a problem for the reasons discussed above.

Other thiophilic ligands coupled to epoxy activated agarose have been disclosed in (J. Porath et. al. Makromol. Chem., Makromol. Symp., vol. 17, p. 359, 1988) and (A. Schwarz et. al., Journal of Chromatography B, vol. 664, pp. 83-88, 1995), e.g. 2-mercaptopyridine, 2-mercaptopyrimidine, and 2-mercaptothiazoline. However, all these affinity matrices still have inadequate affinity constants to ensure an efficient binding of the immunoglobulin without added lyotropic salts.

Liu et al (Yang Liu, Rui Zhao, Dihua Shangguan, Hongwu Zhang, Guoquan Liu: Novel sulfinethazine ligand used for one-step purification of immunoglobulin G from human plasma, Journal of Chromatography B, 792 (2003) 177-185) investigated the affinity of sulfinethazin (SMZ) to human IgG. Thus, a ligand is disclosed, which comprises a sulphonyl group wherein the R group is a heterocyclic ring. According to this article, SMZ was immobilised on monodisperse, non-porous, cross-linked poly(glycidyl methacrylate) beads. The beads were then used in high-performance affinity chromatography for isolation of IgG from human plasma. Maximal adsorption was achieved at pH 5.5. The beads presented minimal non-specific interaction with other proteins. Thus, the ligands were capable of adsorbing antibodies, while their interaction with other proteins was just sufficient to provide retardation thereof in the adsorption buffer used. However, as is well known, ester compounds such as methacrylate are easily hydrolysed at increased pH values. Consequently, similar to Protein A and Protein G matrices, the therein disclosed separation matrix would be expected to unstable at the commonly used cleaning in place (cip) procedures.

U.S. Pat. No. 4,725,355 relates to a body fluid purification medium comprising a support and an adsorbent, which includes at least one sulfa drug, for adsorbing and removing a pathogenic substance in a body fluid. The sulfa drug is a chemotherapeutic agent, and more specifically a sulfonamide characterised by aromatic R group(s). The medium can be provided in a body fluid flow path provided in a container between body fluid inlet and outlet ports.

However, there is still a need of alternative methods for purification of antibodies or immunoglobulin, which observe the demands of purity, safety, potency and cost effectiveness.

BRIEF DESCRIPTION OF THE INVENTION

Accordingly, one aspect of the present invention is a separation matrix, which enables adsorption of immunoglobulins in high amounts. This can be achieved by the separation matrix as defined in claim 1.

Another aspect of the present invention is a separation matrix, which enables highly selective adsorption of immunoglobulins.

A specific aspect of the present invention is a separation matrix to which immunoglobulins are adsorbed, while other proteins are allowed to pass without any substantial interaction.

Further aspects and advantages of the invention will appear from the detailed description that follows.

BRIEF DESCRIPTION OF THE DRAWINGS

FIG. 1 shows the ligand structure of a dimethyl sulfamide ligand.

FIG. 2 shows the separation of α-chymotrypsinogen, lysozyme and ribonuclease as described in Example 3 below. More specifically, a chromatography matrix according to the invention (Prototype IIIs) was packed in a HR 5/5 column (GE Healthcare, Uppsala, Sweden). Separation conditions: The column was equilibrated with the A-buffer for 38 minutes at a flow rate of 0.25 mL/min before the protein mixture was injected. After sample injection (100 μL), a linear gradient from 100% A-buffer to 100% B-buffer was applied. The gradient time was 70 minutes and the flow rate was 0.25 mL/min. A-buffer: 50 mM phosphate buffer (pH 7.0) with 0.80 M $(NH_4)_2SO_4$; B-buffer: 100 mM acetate buffer (pH 4.0)+4% (v/v) IPA. α-chymotrypsinogen and lysozyme are eluted at about 17.85 minutes.

FIG. 3 shows the separation of IgG as described in Example 2 below. More specifically, a chromatography matrix according to the invention (prototype IIIs) was packed in a HR 5/5 column (GE Healthcare, Uppsala, Sweden). Separation conditions: The column (HR 5/5) was equilibrated with the A-buffer for 38 minutes at a flow rate of 0.25 mL/min before the protein mixture was injected. After sample injection (100 μL), a linear gradient from 100% A-buffer to 100% B-buffer was applied. The gradient time was 70 minutes and the flow rate was 0.25 mL/min. A-buffer: 50 mM phosphate buffer (pH 7.0) with 0.80 M $(NH_4)_2SO_4$; B-buffer: 100 mM acetate buffer (pH 4.0)+4% (v/v) IPA. IgG is eluted at 28.73 minutes.

DEFINITIONS

The terms "antibody" and "immunoglobulin" are used herein interchangeably.

The term "ligand" means herein molecules or compounds capable of interaction with target compounds, such as antibodies.

The term "spacer arm" means herein an element that distances a ligand from the support of a separation matrix.

The term "sulfamide" is used herein in its conventional meaning, and an "aliphatic" sulfamide means that none of the R groups is aromatic. Thus, in an "aliphatic" sulfamide, the R groups are either aliphatic groups or hydrogen groups.

A "primary amine" is defined by formula $RNH_2$, wherein R denotes an organic group.

A "secondary amine" is defined by formula $R_2NH$, wherein R denotes an organic group.

The term "eluent" is used in its conventional meaning in this field, i.e. a buffer of suitable pH and/or ionic strength to release one or more compounds from a separation matrix.

DETAILED DESCRIPTION OF THE INVENTION

In a first aspect, the present invention is a separation matrix comprised of a support to which at least one ligand has been immobilised, optionally via a spacer arm, wherein said ligand comprises one or more aliphatic sulfamide groups. In one embodiment, the sulfamide is coupled to the porous support via primary or secondary nitrogen. In an advantageous embodiment, the support is porous.

The present inventors have shown that proteins, such as immunoglobulins, can be purified at a high capacity and with an excellent selectivity using a separation matrix that comprises at least one sulfamide ligands. In this context, it is understood that the term "sulfamide ligands" is used for any ligand that comprises one or more sulfamide groups, as herein described. The separation matrix according to the invention can be used for isolation, such as purification or analysis, of immunoglobulins and other compounds that exhibit equivalent binding properties, such as fusion proteins comprising an immunoglobulin part or immunoglobulin fragments, e.g. Fab fragments.

In one embodiment of the present separation matrix, the sulfamide group is described by the following formula:

$$—N(R_1)—S(O)_2—N(R_2)(R_3) \qquad (I)$$

wherein $R_1$, $R_2$ and $R_3$, independently from each other, are H or linear, optionally branched carbon chains. Thus, $R_1$ may be hydrogen or a linear, optionally branched carbon chain, such as $C_1$-$C_5$. In an advantageous embodiment, $R_1$ is hydrogen.

Similarly, $R_2$ and $R_3$ may, independently from each other, be linear, optionally branched carbon chains. In one embodiment, $R_2$ and $R_3$ are, independently from each other, $C_1$-$C_3$ carbon chains. In this context, it is understood that the carbon chains discussed above may be interrupted by heteroatoms, and/or substituted with any group that does not have any substantial impact on the selectivity of the herein described sulfamide ligands. In one embodiment, $R_2$ and/or $R_3$ are substantially non-hydrophobic groups or polymers, such as polyethylene glycol (PEG). In yet another embodiment, $R_2$ and/or $R_3$ are longer carbon chains that have been rendered substantially non-hydrophobic e.g. by suitable substitution, such as with sugar groups, amino acids or the like. In this context, it is understood that the term "substantially non-hydrophobic" means that the R group does not present such a hydrophobic element as to alter the overall binding characteristics of the present sulfamide ligand.

In a specific embodiment of the present separation matrix, in the sulfamide ligands, the sulfamide groups are present as repetitive units of a polymer immobilised to the support. The polymer may be any suitable polyamine, such as polyalkyleneimine. In one embodiment, the polymer is a polyethylene amine. As the skilled person in this field will realise, the amine content of such a polymer may be varied, e.g. to comprise primary and/or secondary amines in any desired order. Thus, in one embodiment, the polymer exhibit two or more different ligand groups. The polymers are easily produced from suitable monomers according standard methods in this field. Methods of coupling the polyamines to a support are also well known and easily performed by the skilled person in this field, for example by in situ polymerisation or grafting of polymers, see e.g. WO2003/046063. An advantage of this embodiment is that it enables convenient optimisation of the properties of the separation matrix, e.g. by variation of the polymer length, branching etc.

In an advantageous embodiment, the sulfamide ligands have been immobilised to the support via spacer arms, which optionally comprises one or more nitrogen atoms. Spacer arms are well known in the field of chromatography, and the skilled person can easily select a suitable length and chemical composition that improves the separation characteristics of the matrix for sterical reasons.

In one embodiment, the present separation matrix comprises sulfamide ligands which have been evenly or homogenously immobilised to the pore and surface area of the support. As the skilled person will understand, this embodiment encompasses a certain degree of variation due to the immobilisation method, but the aim is to disperse the ligands as evenly as possible. In an alternative embodiment, the ligands have been immobilised to the pore and external surface in a homogenous manner, such as a gradient of ligand densities or as one or more layers of different ligand densities. In a specific embodiment, different sulfamide ligands, as described above, have been coupled to the support in one or more layers.

In a specific embodiment, the present separation matrix comprises, in addition to the sulfamide ligands, other ligands, such as ion exchange ligands or hydrophobic interaction chromatography (HIC) ligands. This is regarded a stochastic separation matrix.

The porous support of the present separation matrix may be of any suitable material. In one embodiment, the support is comprised of a cross-linked carbohydrate material, such as agarose, agar, cellulose, dextran, chitosan, konjac, carrageenan, gellan, alginate etc. The support can easily be prepared according to standard methods, such as inverse suspension gelation (S Hjertén: Biochim Biophys Acta 79(2), 393-398 (1964). Alternatively, the support is a commercially available product, such as SEPHAROSE™ FF (GE Healthcare Bio-Sciences AB, Uppsala, Sweden). Thus, in one embodiment of the present matrix, the support is a cross-linked polysaccharide. In a specific embodiment, said polysaccharide is agarose. Such carbohydrate materials are commonly allylated before immobilisation of ligands thereof. In brief, allylation can be carried out with allyl glycidyl ether, allyl bromide or any other suitable activation agent following standard methods.

In an alternative embodiment, the porous support of the present separation matrix is comprised of cross-linked synthetic polymers, such as styrene or styrene derivatives, divinylbenzene, acrylamides, acrylate esters, methacrylate esters, vinyl esters, vinyl amides etc. Supports of such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare Bio-Sciences AB, Uppsala, Sweden) can be surface-modified according to the invention. However, in this embodiment, the surface of the support is preferably modified to increase its hydrophilicity, usually be converting the majority of the exposed residual double bonds to hydroxyl groups.

In a specific embodiment, the porous support includes a material of a higher density than the rest of the support, such as one or more metal particles. The high density material enables use of the separation material in a fluidised bed process, also known as expanded bed chromatography. In an alternative embodiment, the porous support includes a magnetic material, such as a suitable material, which allows magnetic separation according to well known principles using the separation matrix according to the invention.

The present separation matrix may be provided in any suitable form, such as a chromatography matrix, e.g. in the form of essentially spherical particles or a monolith; a filter or membrane; a chip, a surface, capillaries or the like. Thus, the present invention also encompasses a chromatography column packed with a separation matrix as described above. In an advantageous embodiment, the column is made from any conventional material, such as a biocompatible plastic, e.g. polypropylene, or glass. The column may be of a size suitable for laboratory scale or large-scale purification of antibodies. In a specific embodiment, the column according to the invention is provided with luer adaptors, tubing connectors, and domed nuts. Thus, the present invention also encompasses a kit comprised of a chromatography column packed with a separation matrix as described above; at least one buffer; and written instructions for purification of antibodies in separate compartments. In a specific embodiment, the present kit also comprises luer adaptors, tubing connectors, and domed nuts.

The present separation matrix may be prepared as a disposable product, also known as single use product. Such a disposable separation matrix is advantageously used for the removal of one or more contaminants from a process, in which case the separation is discarded after adsorption of said contaminant. Alternatively, or in addition, the present separation matrix is provided in a sterile form, such as a prepacked chromatography column suitable for use e.g. in the pharmaceutical industry.

An additional aspect of the present invention is a separation material comprising sulfamide ligands in solution phase, such as a buffer or water. The sulfamide ligands may be as discussed above, and are advantageously used to separate target molecules such as immunoglobulins.

In a second aspect, the present invention relates to a process of preparing a separation matrix, which comprises a first step of immobilising amines and/or polyamines to a porous support and a subsequent step of sulfamoylating said amines. Thus, the amines are contacted with a halogenated sulfamoyl, such as dimethyl sulfamoyl chloride. The sulfamoyl reactant may be described by the general formula $Cl-SO_2-N-R_1R_2$. The porous support may be as described above, and any standard methods for immobilisation may be used, see e.g. Immobilized Affinity Ligand Techniques, Hermanson et al, Greg T. Hermanson, A. Krishna Mallia and Paul K. Smith, Academic Press, Inc., 1992. However, as the skilled person in this field will realise, some of the separation matrices may equally well be prepared by immobilisation of sulfamides directly to the support, depending on the nature of the ligand. An alternative embodiment of the second aspect of the invention is a process wherein a partially sulfamoylated polyamine is coupled to an activated porous support, such as an epoxidated support.

In a third aspect, the present invention is a method of isolating at least one immunoglobulin from a liquid, which method comprises the steps of (a) providing a liquid that comprises at least one immunoglobulin:

(b) contacting said liquid with a separation matrix comprising one or more sulfamide groups, whereby one or more immunoglobulins are adsorbed to said matrix; and, optionally, (c) passing an eluent over said matrix to release one or more immunoglobulins; and (d) recovering at least one immunoglobulin from the eluent.

In this context, it is to be understood that the term "immunoglobulin" also includes fragments, such as Fab fragments, any fusion protein that comprises an immunoglobulin or a fragment thereof, as well as scFv (single chain variable fragments), nanobodies, diabodies, triabodies, minibodies etc. Thus, the present method is useful to isolate such immunoglobulin-like molecules, which present the binding properties of an immunoglobulin. The liquid comprising an immunoglobulin may for example be a liquid originating from a cell culture producing antibodies or a fermentation broth, from which it is desired to purify one or more desired antibodies. Alternatively, the liquid may be blood or blood plasma, from which it is desired to remove one or more antibodies to obtain a liquid which is pure in that respect. Thus, in one embodiment of the present method, the liquid provided in step (a) also comprises one or more other proteins than immunoglobulins. As will be shown in the experimental part below, in general, the present method allows selective adsorption of antibodies at relatively low ionic strengths. Unexpectedly, the present inventors found that the use of a porous separation matrix that exhibits one or more sulfamide groups enables the strong adsorption of immunoglobulins while other proteins are more weakly adsorbed, or not adsorbed at all. Accordingly, the present method provides pure preparations of antibodies in high yields. The skilled person in this field can easily select the optimal conditions for each sulfamide ligand structure using routine experimentation, as will be discussed in the experimental part below. For example, it is well known in this field that properties of a separation matrix can be optimised by variation of either the nature of the gel; in this case, the R group of the sulfamide, or the degree of substitution i.e. the ligand density on the support. The salt concentration in the adsorption buffer can also be optimised for each ligand. Thus, in one embodiment of the present invention, the adsorption of step (b) is provided at a salt concentration of about 0.25 M $Na_2SO_4$. In a specific embodiment, the ligands comprise monoamines, and step (b) is performed at a salt concentration above about 0.5 M $Na_2SO_4$.

The present method can use a separation matrix in any suitable form, such as a chromatography matrix, e.g. in the form of essentially spherical particles or a monolith; a filter or membrane; a chip or the like. Thus, in an advantageous embodiment, the separation matrix of step (b) is provided in a chromatography column.

The support and the ligands of the separation matrix of step (b) may be anyone of the ones described above.

As mentioned above, the present invention has unexpectedly shown that using the novel separation matrix according to the invention enables highly selective adsorption of immunoglobulins at a neutral pH. Thus, in one embodiment, step (b) is performed at a pH of 6.5-8.3, such around 7.

In an advantageous embodiment, the elution of step (c) is performed by an adjustment of the pH, such as a decrease or increase of pH. A pH adjustment can also be combined with a salt gradient. In a specific embodiment, step (b) is performed at neutral or close to neutral pH, and step (c) is a gradient elution performed by adding an eluent of decreasing pH.

In an alternative embodiment, step (c) is a gradient elution performed by adding an eluent of decreasing salt concentration to the separation matrix, preferably by passing said eluent over the matrix. The gradient may be of any shape, such as a linear or stepwise gradient. Other elution schemes are also useful, such as adding a competitive binder in the eluent, adding to the eluent a compound that displaces the adsorbed antibodies on the matrix, such as Protein A, which is a well known immunoglobulin-binder, a sulfamide with binding properties that differ from the sulfamide ligand etc, or providing a temperature change etc.

The present method is useful to recover any kind of monoclonal or polyclonal antibody, such as antibodies originating from mammalian hosts, such as mice, rodents, primates and humans, or antibodies originating from cultured cells such as hybridomas. In one embodiment, the antibodies recovered in step (d) are human or humanised antibodies. The antibodies may be of any class, i.e. selected from the group that consists of IgA, IgD, IgE, IgG, and IgM. In a specific embodiment, the antibodies recovered in step (d) are immunoglobulin G (IgG). The present invention also encompasses the purification of fragments of any one of the above mentioned antibodies as well as fusion proteins comprising such antibodies.

An advantageous application of the sulfamide separation matrix according to the invention is found in preparation of an immunoglobulin-containing sample, wherein the sulfamide ligand is used to reduce sample complexity e.g. to allow detection of presence, or determining the level, of a specific target, for example before electrophoresis. Thus, in one embodiment, the present invention relates to the use of sulfamide ligands, advantageously coupled to a porous or nonporous support, in a process for reducing sample complexity. In an advantageous embodiment, the separation matrix according to the invention is used, and some undesired material, such as DNA and/or RNA, pass the column while other material such as certain host cell proteins bind weakly to the column and the target immunoglobulin binds more strongly and hence can be eluted selectively.

The present method allows quantitative adsorption of antibodies. Thus, in one embodiment, the present method encompasses a method as defined above and in addition a step (e) of determining the amount of immunoglobulin spectrophotometrically. Such methods and useful equipment are well known to the skilled person in this field. The sulfamide ligands according to the invention are also useful in analytical procedures, e.g. immobilised to a surface, which may be porous or non-porous. In a specific embodiment, this aspect of the invention is a biosensor comprising sulfamide ligands as described above, which allows specific detection of one or more immunoglobulins. In an advantageous embodiment, the biosensor allows specific detection of one or more Fab fragments.

EXAMPLES

The present examples are presented herein for illustrative purpose only, and should not be constructed to limit the invention as defined by the appended claims.

Example 1

Preparation of a Dimethyl Sulfamide Separation Matrix

General

Volumes of matrix refer to settled bed volume and weights of matrix given in gram refer to suction dry weight. For large scale reaction stirring is referring to a suspended, motor-driven stirrer since the use of magnet bar stirrer is prompt to damage the beads. Small-scale reactions (up to 20 mL or g of gel) were performed in closed vials and stirring refers to the use of a shaking table. Conventional methods were used for the analysis of the functionality and the determination of the degree of allylation, or the degree of amine content on the beads.

One way to prepare a separation matrix according to the invention is exemplified below, starting from a crosslinked agarose gel (SEPHAROSE™ 6 Fast Flow, GE Healthcare, Uppsala, Sweden). Production of six dimethyl sulfamide prototypes (Is-VIs) with different ligand density is presented below and the ligand structure of these prototypes is depicted in FIG. 1.

A. Allyl Activation with Allylglycidylether 100 mL of drained SEPHAROSE™ 6 Fast Flow were transferred to a reaction vessel and distilled water, 50% NaOH and $Na_2SO_4$ were added. Six prototypes were produced according to Table 1. After 1 h of stirring at 50° C. allylglycidylether (AGE) was added according to Table 1. The reaction slurry was stirred at 50° C. for 18 h followed by washing on a glass filter funnel with distilled water, ethanol and finally distilled water. Allyl content was measured by titration (Table 1).

TABLE 1

Reaction conditions for production of 6 different allylated SEPHAROSE ™ 6 Fast Flow (prototypes: I-VI).

| Proto-type | SEPHAROSE ™ 6FF (mL) | Dist. water (mL) | 50% NaOH (mL) | $Na_2SO_4$ (g) | AGE (mL) | Allyl content (μmol/mL) |
|---|---|---|---|---|---|---|
| I | 100 | 29 | 14 | 0 | 55 | 77 |
| II | 100 | 13 | 31 | 0 | 55 | 109 |
| III | 100 | 3 | 40 | 0 | 55 | 134 |
| IV | 100 | 3 | 40 | 0 | 65 | 158 |
| V | 100 | 20 | 35 | 12 | 100 | 214 |
| VI | 100 | 25 | 90 | 12 | 100 | 420 |

B. Coupling with Cysteamine 50 mL of drained allylated SEPHAROSE™ 6 Fast Flow was thoroughly washed with 2-propanol. The gel was stirred in a capped vessel in a total volume of 95 mL of 2-propanol and with 8 equivalents of cysteamine-HCl at 70° C. After 20 minutes 0.4 equivalents of 2,2'-azobis(2-methylbutyronitrile) was added and after 4 hours a second 0.4 equivalents portion of 2,2'-azobis(2-methylbutyronitrile) was added to the reaction slurry.

After a total of 16 hours reaction time the gel was washed on a glass filter with 2-propanol followed by ethanol and water. The amine content was determined by titration and is presented in Table 2 for all six prototypes (Ia-VIa).

TABLE 2

Amine content of the six semi products (Ia-IVa) after coupling of cysteamine to the allylated SEPHAROSE ™ 6 Fast Flow prototypes (I-IV).

| Cysteamine prototype | Allyl prototype | Amine content (μmol/mL) |
|---|---|---|
| Ia | I | 73 |
| IIa | II | 108 |
| IIIa | III | 136 |
| IVa | IV | 166 |
| Va | V | 230 |
| VIa | VI | 350 |

C. Derivatization with Dimethylsulfamoyl Chloride 6 g quantity of cysteamine coupled gel was washed with 3×10 mL ethanol followed by 3×10 mL DCM (dichloromethane). The gel was transferred to a vial plus 3 mL DCM plus 3.2 equivalents of N,N-diisopropylethylamine (DIPEA) and stirred for 5 minutes. After drop wise adding of 3 equivalents of dimethylsulfamoylchloride, the reaction mixture was stirred at room temperature for 18 hours.

After filtration of the reaction mixture the gel was successively washed with 3×15 mL DCM, 3×15 mL ethanol, 3×15 mL distilled water, 3×15 mL 0.2 M NaOH and finally with 3×15 mL of distilled water. Remaining amines were quantified by titration and the amount of sulfamide content was calculated according to Table 3.

TABLE 3

Sulfamide content of the six prototypes (Is-IVs) after coupling of dimethylsulfamoylchloride to the cysteamine SEPHAROSE ™ 6 Fast Flow prototypes (Ia-IVa).

| Prototype | Amine content in sulfamide prototypes (μmol/mL) | Sulfamide content (μmol/mL) | Cysteamine prototype | Amine content of cysteamin prototype (μmol/mL) |
|---|---|---|---|---|
| Is | 20 | 53 | Ia | 73 |
| IIs | 21 | 87 | IIa | 108 |
| IIIs | 23 | 113 | IIIa | 136 |
| IVs | 20 | 146 | IVa | 166 |
| Vs | 18 | 212 | Va | 230 |
| VIs | 13 | 337 | VIa | 350 |

Example 2

Selective Adsorption of IgG

To test if the sulfamide prototypes according to the invention adsorb human immunoglobulin (IgG) selectively, the breakthrough capacity of IgG and BSA was tested. The sulfamide prototypes (Is-VIs) were packed in HR 5/5 columns and the sample solution was pumped at a flow rate of 0.5 mL/min through the column after equilibration with buffer solution. The breakthrough capacity was evaluated at 10% of the maximum UV detector signal (280 nm). The maximum UV signal was estimated by pumping the test solution directly into the detector. The breakthrough capacity at 10% of absorbance maximum ($Q_{b10\%}$) was calculated according to the formula:

$$Q_{b10\%} = (T_{R10\%} - T_{RD}) \times C/V_c$$

where $T_{R10\%}$ is the retention time (min) at 10% of absorbance maximum, $T_{RD}$ the void volume time in the system (min), C the concentration of the sample (4 mg protein/mL) and $V_C$ the column volume (mL). The adsorption buffer used at breakthrough capacity measurements was 20 mM phosphate (pH 7.4) with 0.5 M Na$_2$SO$_4$.

Sample

The samples used for breakthrough measurements were human immunoglobulin (IgG, Gammanorm) and bovine serum albumine (BSA). The proteins were dissolved in the adsorption buffers at a concentration of 4 mg/mL and only one protein at a time was applied into the column.

Instrumental

| Apparatus | |
|---|---|
| LC System: | ÄKTA EXPLORER ™ 10 XT or equal |
| Software: | UNICORN ™ |
| Column: | HR 5/5 |

Instrument Parameters

| | |
|---|---|
| Flow rate: | 0.5 mL/min |
| Detector cell: | 10 mm |
| Wavelength: | 280 nm |

UNICORN™ Method

The main method used at breakthrough experiments is depicted below:
0.00 Base CV 0.50 {mL} #Column volume {mL} Any
0.00 Block Start conditions
    0.00 Base SameAsMain
    0.00 Wave length 280 {nm} 254 {nm} 215 {nm}
    0.00 AvaragingTime 2.56 {sec}
    0.00 Alarm Pressure Enable 3.00 {MPa} 0.00 {MPa}
    0.00 End Block
0.00 Block Column position
0.00 Block Equilibration
    0.00 Base SameAsMain
    0.00 PumpAInlet A1
    0.00 BufferValveA1 A11
    0.00 Flow 0.5 {mL/min}
    1.00 Set Mark ( )#column name
    3.9 AutoZeroUV
    5.0 #Equilibration volume End Block
0.00 Block Sample loading
    0.00 Base volume
    0.00 Flow (1)#flow rate {mL/min}
    0.00 Set Mark ( )#sample
    0.00 InjectionValve Inject
    0.00 Watch UV Greater Than (100) #20 percent maxabs {mAu} END BLOCK
    49.00 InjectionValve Load
    49.00 End Block
0.00 Block Column wash
    0.00 Base SameAsMain
    0.00 InjectionValve Load
    0.00 Watch Off UV
    0.00 PumpAInlet A1
    0.00 BufferValveA1 A11
    0.00 Watch UV Less Than (20) #5 percent {mAu} END BLOCK
    20.00 End Block
0.00 Block Gradient elution
    0.00 Base SameAsMain
    0.00 PumpBInlet B1
    0.00 Gradient 100 {% B} 2.00 {base}
    0.00 Flow 0.50 {mL/min}
    10.00 Gradient 0.00 {% B} 0.00 {base}
    10.00 End Block
0 Block Reequilibration
    0.00 End Method Results and Discussion An ideal adsorbent for immunoglobulin must not only have a significant selectivity but should also be able to adsorb high amounts of immunoglobulins (IgG). As a measure of selectivity the ratio ($Q_{b10}$IgG/$Q_{b10}$ BSA) can be utilized. A high value of this ratio means that IgG is adsorbed but not BSA when a sample solution consisting of both proteins is applied to the column. In Table 4 the breakthrough values ($Q_{b10}$) of IgG and BSA for all sulfamide prototypes (Is-VIs) are presented. All prototypes except Is has a very high selectivity for IgG (high value of $Q_{b10}$ IgG/$Q_{b10}$ BSA). Prototype Is has the lowest ligand density of the six prototypes (Table 3) and also a very low breakthrough capacity of IgG (Table 4). The most optimal prototypes with respect to selectivity are IIIs and IVs. Prototype IVs has the highest breakthrough capacity for IgG of these two prototypes. These results indicate that a ligand density of about 150 μmol/mL (Table 3) is optimal with respect to selectivity and IgG capacity.

TABLE 4

Breakthrough capacity ($Q_{b10}$) of IgG and BSA for six different prototypes packed in HR 5/5 columns.

| Prototype | $Q_{b10}$ IgG[1] (mg/mL) | $Q_{b10}$ BSA[1] (mg/mL) |
|---|---|---|
| Is | 2.8 | 1.8 |
| IIs | 9.3 | 0 |
| IIIs | 26.9 | 1.0 |
| IVs | 36.2 | 1.5 |
| Vs | 38.0 | 4.1 |
| VIs | 33.4 | 4.8 |

[1]Adsorption buffer: 20 mM phosphate buffer (pH = 7.4) with 0.5 M Na$_2$SO$_4$; Desorption buffer: 100 mM acetate buffer (pH = 4.0); Flow rate: 0.5 ml/min Example 3

Separation of α-Chymotrypsinogen, Cytochrome C, Ribonuclease and IgG

In order to document the selectivity of sulfamide ligands towards IgG a number of other proteins were investigated. In this investigation four proteins (α-chymotrypsinogen, lysozyme, ribonuclease and IgG) were used to more carefully prove that IgG interacts more strongly with sulfamide ligands than other proteins. The binding and elution of the proteins were done with normal chromatographic operating procedures. In FIG. 2 the separation of α-chymotrypsinogen, lysozyme and ribonuclease is presented. The last eluted proteins (α-chymotrypsinogen and lysozyme) eluted at about 17.85 minutes. In FIG. 3 it is shown that IgG is eluted at 28.73 min using the same chromatographic conditions as in FIG. 2. The results clearly show that of the four investigated proteins the sulfamide ligand interacts strongest with IgG. This is manifested by a longer retention time of IgG compared to the other proteins (FIGS. 1 and 2).

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A separation matrix comprised of a support to which at least one ligand has been covalently immobilized, optionally via a spacer arm, wherein said ligand comprises one aliphatic sulfamide group described by the following formula:

$$-N(R_1)-S(O)_2-N(R_2)(R_3) \qquad (I)$$

wherein $R_1$, $R_2$ and $R_3$ are, independently from each other, either hydrogen or linear, optionally branched carbon chains, and wherein the content of aliphatic sulfamide groups is 113-337 micromol/ml.

2. The matrix of claim 1, wherein the support is porous.

3. The matrix of claim 1, wherein $R_1$ is hydrogen.

4. The matrix of claim 1, wherein $R_2$ and/or $R_3$ are C1-C3 carbon chains.

5. The matrix of claim 1, wherein $R_1$=H and $R_2$=$R_3$=$CH_3$ having the following structure

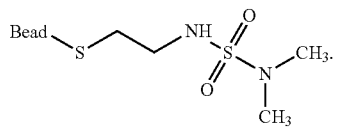

6. The matrix of claim 1, wherein the sulfamide groups are present as repetitive units of a polymer covalently immobilized to the support.

7. The matrix of claim 1, which comprises sulfamide ligands coupled to a support via spacer arms, which optionally comprises one or more nitrogen atoms.

8. The matrix of claim 1, further comprising ion exchange ligands or hydrophobic interaction chromatography (HIC) ligands.

9. The matrix of claim 1, wherein the support is a cross-linked polysaccharide.

10. The separation matrix of claim 1 in a solution phase.

11. A chromatography column packed with the separation matrix of claim 1.

12. The chromatography column of claim 11, which is substantially sterile.

13. The chromatography column of claim 11, which is a disposable product.

14. A process of preparing the separation matrix of claim 1, said method comprises a first step of covalently immobilizing amines to a support and a subsequent step of sulfamoylating said amines to provide aliphatic sulphamide ligands.

15. The process of claim 14, wherein the amines and/or polyamines are covalently immobilized to the support via spacer arms.

16. A method of isolating at least one immunoglobulin from a liquid, which method comprises the steps of:
    (a) providing a liquid that comprises at least one immunoglobulin:
    (b) contacting said liquid with aliphatic sulfamide ligands to adsorb one or more immunoglobulins to the matrix of claim 1 containing said aliphatic sulfamide ligands; and, optionally,
    (c) contacting said matrix with an eluent to release one or more immunoglobulins; and
    (d) recovering at least one immunoglobulin.

17. The method of claim 16, wherein the liquid provided in step (a) also comprises one or more other proteins.

18. The method of claim 16, wherein the separation matrix of step (b) is provided in a chromatography column.

19. The method of claim 16, wherein step (b) is performed at a neutral or close to neutral pH.

20. The method of claim 16, wherein step (c) is a gradient elution performed by passing an eluent of decreasing pH across the matrix.

21. The method of claim 16, wherein the immunoglobulins recovered in step (d) are human or humanised immunoglobulins.

22. The method of claim 21, wherein the immunoglobulins recovered in step (d) are immunoglobulin G (IgG).

23. A method of determining the quantity of an immunoglobulin, which method encompass the method of claim 16 and in addition a step (e) of determining the amount of immunoglobulin spectrophotometrically.

* * * * *